United States Patent
Boissonneault et al.

(10) Patent No.: US 12,138,270 B2
(45) Date of Patent: Nov. 12, 2024

(54) CONTRACEPTIVE REGIMEN INCLUDING REDUCED LEVEL OF ESTROGEN

(71) Applicant: Millicent Pharma Limited, Dundalk (IE)

(72) Inventors: Roger M. Boissonneault, Branford, CT (US); Ryan Loughlin, Banbridge (GB)

(73) Assignee: Millicent Pharma Limited, Dundalk (IE)

( * ) Notice: Subject to any disclaimer, the term of this patent is extended or adjusted under 35 U.S.C. 154(b) by 0 days.

(21) Appl. No.: 17/483,199

(22) Filed: Sep. 23, 2021

(65) Prior Publication Data
US 2023/0070977 A1    Mar. 9, 2023

Related U.S. Application Data

(60) Provisional application No. 63/241,178, filed on Sep. 7, 2021.

(51) Int. Cl.
*A61K 31/565*    (2006.01)
*A61K 31/57*    (2006.01)

(52) U.S. Cl.
CPC .......... *A61K 31/565* (2013.01); *A61K 31/57* (2013.01)

(58) Field of Classification Search
CPC ............................ A61K 31/565; A61K 31/57
See application file for complete search history.

(56) References Cited

U.S. PATENT DOCUMENTS

| | | |
|---|---|---|
| 4,826,831 A | 5/1989 | Plunkett et al. |
| 4,962,098 A | 10/1990 | Boissonneault |
| 5,208,225 A | 5/1993 | Boissonneault et al. |
| 5,552,394 A * | 9/1996 | Hodgen ............... A61K 31/567 514/843 |
| 5,888,543 A | 3/1999 | Gast |
| 5,898,032 A | 4/1999 | Hodgen |
| 7,704,983 B1 | 4/2010 | Hodgen et al. |
| 8,124,595 B2 | 2/2012 | Boissonneault |
| 8,461,138 B2 | 6/2013 | Boissonneault |
| 9,132,137 B2 | 9/2015 | Boissonneault |
| 2002/0177580 A1 | 11/2002 | Van Beek et al. |
| 2005/0250747 A1 | 11/2005 | Sachse |
| 2006/0241092 A1* | 10/2006 | Anderson ............... A61K 31/56 514/170 |
| 2007/0111975 A1 | 5/2007 | Diliberti et al. |

FOREIGN PATENT DOCUMENTS

| | | |
|---|---|---|
| EP | 0 226 679 B1 | 7/1987 |
| EP | 0911029 A2 | 4/1999 |
| EP | 2 029 146 B1 | 3/2009 |
| WO | 2010/033188 A2 | 3/2010 |
| WO | 2021/260511 A1 | 12/2021 |

OTHER PUBLICATIONS

Jenny Brotherston, "Contraception meets HRT: seeking optimal management of the perimenopause," British Journal of General Practice, vol. 65, No. 638, pp. e630-e632 (Sep. 2015).
Americanpharmawholesale.com, "Rx Item-Norethin-Eth Estra 0.5Mg-2.5Mcg Tab 3X28 By Nivagen Pharma FYAVOLV," Dec. 11, 2018. Label: Norethindrone Acetate and Ethinyl Estradiol Tablet, Dec. 11, 2018.
Rowan et al., "Effects of Low-Dose Norethindrone Acetate Plus Ethinyl Estradiol (0.5 mg/2.5 ug) in Women with Postmenopausal Symptoms: Updated Analysis of Three Randomized Controlled Trials," Clinical Therapeutics, vol. 28, pp. 921-932 (2006).
Archer et al., "Norethindrone Acetate 1.0 Milligram and Ethinyl Estradiol 10 Micrograms as an Ultra Low-Dose Oral Contraceptive," Obstetrics and Gynecology, vol. 122, pp. 601-607 (2013).
Invitation to Pay Additional Fees in International Application No. PCT/IB2022/058420 (Nov. 2022).

* cited by examiner

*Primary Examiner* — Craig D Ricci
*Assistant Examiner* — Janet L Coppins
(74) *Attorney, Agent, or Firm* — Venable LLP

(57) ABSTRACT

A contraceptive regimen that provides for a reduced level of estrogen. The contraceptive regimen can be used for the treatment of symptoms associated with endometriosis or fibroids.

11 Claims, No Drawings

CONTRACEPTIVE REGIMEN INCLUDING REDUCED LEVEL OF ESTROGEN

The present application claims the benefit of U.S. Provisional Application No. 63/241,178, filed Sep. 7, 2021, the entirety of which is incorporated by reference herein.

FIELD OF THE INVENTION

This invention is related to regimens that include a progestogenic and estrogenic components that can be used for contraception and provide not only significantly less estrogen daily, but also significantly less overall estrogen in the regimen without compromising contraceptive efficacy, cycle control, or other desired benefits. Moreover, the invention provides for regimens that are effective for contraception while reducing the risk for osteoporosis. In addition, the regimens provided herein can be used for the treatment of one or more symptoms associated with endometriosis or fibroids. Also provided is a kit that may be used to practice the aforementioned inventive regimens.

BACKGROUND OF THE INVENTION

Contraceptive compositions typically contain both estrogenic and progestogenic compounds and are known to be highly effective in controlling ovulation. The progestogenic component of the composition is primarily responsible for the contraceptive efficacy of the composition, and the estrogenic component is employed to reduce undesired side effects, such as breakthrough bleeding, spotting, or bone loss.

Earlier forms of estrogenic/progestogenic contraceptive compositions (monophasic or multiphasic) contained a relatively high level of estrogenic component. Over time estrogenic/progestogenic contraceptive compositions have been disclosed where the amount of estrogen of such compositions has been lowered without reducing contraceptive efficacy and/or increasing undesired side effects. U.S. Pat. No. 5,888,543, discloses progestogen/estrogen combinations in a monophasic regimen (fixed dose in the cycle) or as biphasic or triphasic regimens (varied dose over the cycle).

U.S. Pat. No. 4,962,098 discloses a triphasic method of contraception using a progestogen/estrogen combination in which the amount of estrogen is increased stepwise over the three phases. For all three phases the progestogen is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase. Other multiphasic contraceptive compositions have been described in U.S. Pat. Nos. 8,461,138 and 8,124,595.

Alternatively, another form of contraception, known as "mini-pills" only contains progestogen component in the absence of the estrogenic component. While this may not have certain drawbacks associated with estrogen exposure, it is known to induce bone loss and have less contraceptive efficacy than that of a combined estrogenic/progestogenic contraceptive composition.

SUMMARY OF THE INVENTION

The invention provides both cyclic and continuous methods of contraception that make it possible to significantly reduce not only the daily amount of estrogen administered, but also the overall amount of estrogen administered, while still achieving desired contraceptive efficacy and controlling undesired side effects. In addition, the regimens disclosed herein can be used for the treatment of one or more symptoms associated with endometriosis or fibroids.

This invention is related to a method of contraception for a female in need thereof. In an embodiment, the method is a cyclic monophasic method and comprises the step of: administering, daily, about 1 mcg to less than about 5 mcg of an estrogen and 0.075 mg to about 5 mg of a progestogen for about 20 to about 27 consecutive days of a 28-day cycle. The method comprises the step of administering, daily, a placebo for a remainder of the 28-day cycle.

In an embodiment, the method is a cyclic multiphasic method and comprises the steps of: administering, daily, about 1 mcg to less than about 5 mcg of an estrogen and 0.075 mg to about 5 mg of a progestogen for about 20 to about 26 consecutive days of a 28-day cycle; and administering, daily, about 1 mcg to less than about 5 mcg of the estrogen in the absence of the progestogen for about 1 to about 6 consecutive days, of the 28-day cycle following the preceding step. The method comprises the step of administering, daily, a placebo for a remainder of the 28-day cycle.

In an embodiment, the method is a cyclic monophasic method and comprises the step of: administering, daily, about 1 mcg to less than about 5 mcg of an estrogen and 0.075 mg to about 5 mg of a progestogen for at least about 28 consecutive days up to about 84 consecutive days of a cycle. The method comprises the step of administering, daily, a placebo for about 1 to 7 consecutive days of the cycle.

In an embodiment, the method is monophasic continuous method and comprises the step of administering, daily about 1 mcg to less than about 5 mcg of an estrogen and 0.075 mg to about 5 mg of a progestogen.

DETAILED DESCRIPTION OF THE INVENTION

The regimens disclosed herein can be used for contraception, which, in addition to providing desired contraceptive efficacy, can control undesired side effects associated with conventional contraceptive regimens. The regimens disclosed herein can also provide effective treatment or prevention of symptoms related to endometriosis or fibroids, such as pain and heavy bleeding. As a result, there is no need for a separate treatment of these symptoms, such as conventionally prescribed GnRH antagonists or agonists.

Conventional contraceptive regimens utilize relatively high amounts of estrogen. While these amounts are less than what they were even a few decades ago, they are still sufficiently high to have the potential to cause various adverse effects. From among the currently available combined estrogenic/progestogenic contraceptive regimens, Lo Loestrin® has the lowest level of estrogen at 10 mcg of ethinyl estradiol per day. However, even this amount of estrogen can contribute to endometrial tissue stimulation and may lead to adverse effects including inflammation, severe pain, heavy or light periods, aggravated premenstrual syndrome, weight gain, noncancerous lumps in breasts, fibroids, fatigue, low sex drive, depression, or anxiety. Especially for females with endometriosis, which is a chronic disorder characterized by the implantation of endometrial glands and stroma outside the uterine cavity, these symptoms can be more severe and debilitating.

While there are different hypotheses regarding the pathogenesis of endometriosis, one conventional way to treat the symptoms of endometriosis is by administering either GnRH agonists or GnRH antagonists. For example, GnRH antagonists, such as elagolix, are typically prescribed for the management of moderate to severe pain associated with endometriosis in pre-menopausal females. However, these GnRH antagonists reduce endogenous sex hormones, such as estrogens, to post-menopausal levels. This can lead to a reduction in bone density, the occurrence of post-menopausal vasomotor systems, such as hot flashes or night sweats, and other urogenital symptoms. As a result, combinations of an estrogen and progestogen are often prescribed concomitantly with GnRH antagonists to treat the side effects of pharmacologically induced menopause, and since GnRH antagonists are not prescribed for contraception.

An alternative available contraceptive regimen is, for example, a so-called "mini-pill," which only includes a progestogenic component in order to avoid some of the drawbacks associated with estrogen exposure. For example, a mini-pill may be prescribed to females who are breast-feeding. Moreover, as females begin to get closer to peri-menopause or menopause, doctors may prescribe the mini-pill rather than a conventional contraceptive regimen, since conventional contraceptive regimens are not recommended to be prescribed with conditions such as high blood pressure, cardiovascular issue, as well as issues with mobility. However, the absence of estrogen altogether has its own drawbacks because an estrogenic component in a contraceptive can be helpful for decreasing the effects of bone loss, increasing stability to the endometrium, preventing irregular shedding and unwanted breakthrough bleeding as well as increasing the potency of the progestogenic component including in its antifertility effects.

In contrast, the present invention provides estrogenic/progestogenic regimens that use a significantly lower amount of estrogenic component than conventional contraceptive regimens, yet provide more benefits than the "mini-pill." Advantageously, as a result of the reduction in the overall level of estrogenic compound exposure over the complete cycle, the endometrial tissue stimulation can be reduced or minimized. Thus, the regimens disclosed herein can be used not only for contraception, but also to treat the symptoms associated with endometriosis and/or fibroids without the need for administering a conventional treatment, such as a GnRH antagonist or agonist. In addition, the overall significantly reduced level of estrogenic compound exposure only minimally contributes to bone loss and, surprisingly, may have little to no effect on suppression of lactation. Furthermore, described herein are regimens that allow for safe, effective and long-term use without a placebo, which can eliminate the withdrawal bleed, and allows for a female to remain on the same regimen, without needing to switch to, for example, a mini-pill, when closer in age to peri-menopause or menopause. The regimens disclosed herein are also safe and effective for females who may have cardiovascular issues and/or high blood pressure.

The designation "mcg" refers to micrograms and "mg" to milligrams.

The term "administration" refers to oral administration. That is, the methods/regimens disclosed herein pertain to oral administrations.

The term "female in need thereof" refers to a female of child-bearing age, and may be experiencing one or more symptoms associated with endometriosis or fibroids. For example, the female in need thereof is a female who has started menstruation and/or is sexually active but is not yet in menopause. Thus, the female in need thereof is pre-menopausal or peri-menopausal, but not in menopause, such that the age range may be about 14 years old to about 55 years old, depending on the individual.

The term "continuous" refers to the uninterrupted time period of hormone administration in which there are no hormonal component-free intervals (i.e., placebo periods). Thus, a continuous period, which may be up to about 40 years, does not have a time interval which induces a withdrawal bleed for the duration of the method.

The symptoms associated with endometriosis or fibroids include, for example, pain, menstrual symptoms, gastrointestinal symptoms, abdominal symptoms, and infertility. Pain associated with endometriosis can include, for example, lower abdominal pain, lower back pain, pelvic pain, rectal pain, and vaginal pain. Pain associated with endometriosis can also include, for example, pain during sexual intercourse, pain during defecation, and pain during urination. Menstrual symptoms associated with endometriosis can include, for example, abnormal menstruation, heavy menstruation, irregular menstruation, prolonged menstruation, painful menstruation, and spotting. Gastrointestinal symptoms associated with endometriosis include, for example, diarrhea, constipation, and nausea. Abdominal symptoms associated with endometriosis can include, for example, abdominal fullness and cramping. One of ordinary skill in the art would recognize that the amount of pain the female in need thereof experiences does not necessarily correlate with the severity of endometriosis. For example, on the one hand, the female in need thereof having a moderate or severe degree of endometriosis may experience minimal or no pain. On the other hand, the female in need thereof having a mild degree of endometriosis may experience moderate or severe pain or other aforementioned symptoms associated with endometriosis.

Endometriosis can be located in various parts of the female in need thereof, including, for example, ovaries, fallopian tubes, uterosacral ligaments, posterior cul-de-sac (space between the uterus and rectum), anterior cul-de-sac (space between the uterus and bladder), outer surface of the uterus, lining of the pelvic cavity, intestines, rectum, bladder, vagina, cervix, vulva, and abdominal surgery scars.

Estrogens which may be used in the present invention include, for example, ethinyl estradiol, 17β-estradiol, 17β-estradiol-3-acetate, mestranol, conjugated estrogens, USP and estrone or salts thereof. In an embodiment, the estrogen is ethinyl estradiol. The amount of estrogen used is described herein as that which is "equivalent" in estrogenic potency to an amount of ethinyl estradiol. The equivalent estrogenic potency of an estrogen to ethinyl estradiol may be readily determined by one of ordinary skill in the art.

Progestogens which may be used in the present invention include, for example, progesterone and its derivatives such as 17-hydroxy progesterone esters and 19-nor-17-hydroxy progesterone esters, 17-alpha-ethinyl testosterone, 17-alpha-ethinyl-19-nortestosterone (norethindrone) and derivatives thereof, norethindrone acetate, norgestrel, nogestamate, desogestrel and D-17-beta-acetoxy-17-beta-ethyl-17-alpha-ethinyl-gon-4-en-3-one oxime. Other exemplary progestogens include demegestone, drospirenone, dydrogesterone, gestodene, medrogestone, medroxy progesterone and esters thereof. The amount of progestogen used is described herein as that which is "equivalent" in progestogenic potency to an amount of norethindrone acetate. The equivalent progestogenic potency of a progestogen to norethindrone acetate may be readily determined by one of ordinary skill in the art.

In the regimens discloses herein, a placebo may be skipped altogether so that neither the active ingredients nor a placebo composition (e.g., a sugar tablet) is administered.

That is, a reference to the administration of a placebo herein also encompasses skipping altogether the active ingredients and the placebo composition.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for about 20 to about 27 consecutive days of a 28-day cycle; and (b) a placebo for the remainder of the 28-day cycle. The administration period for this monophasic cyclic contraceptive method is based on a 28-day cycle. In an embodiment, a new cycle begins following the completion of the preceding cycle. For example, a new 28-day cycle begins following the completion of the preceding 28-day cycle. In an embodiment, the new cycle and the preceding cycle are identical in the number of days In an embodiment, the estrogen is administered in a daily amount of about 1.0 mcg to less than about 5.0 mcg. In an embodiment, the estrogen is administered in a daily amount of about 2.0 mcg to about 4.0 mcg, or about 2.25 mcg to about 3.5 mcg, or about 2.25 mcg to about 3.0 mcg. In an embodiment, the estrogen is administered in a daily amount of about 1 mcg, or about 1.1 mcg, or about 1.2 mcg, or about 1.3 mcg, or about 1.4 mcg, or about 1.5 mcg, or about 1.6 mcg, or about 1.7 mcg, or about 1.8 mcg, or about 1.9 mcg, or about 2.0 mcg, or about 2.1 mcg or about 2.2 mcg, or about 2.3 mcg, or about 2.4 mcg, or about 2.5 mcg, or about 2.6 mcg, or about 2.7 mcg, or about 2.8 mcg, or about 2.9 mcg, or about 3.0 mcg, or about 3.1 mcg or about 3.2 mcg, or about 3.3 mcg, or about 3.4 mcg, or about 3.5 mcg, or about 3.6 mcg, or about 3.7 mcg, or about 3.8 mcg, or about 3.9 mcg, or about 4.0 mcg or about 4.1 mcg, or about 4.2 mcg, or about 4.3 mcg, or 4.4 mcg, or about 4.5 mcg, or any amount in between. In an embodiment, the estrogen is administered in a daily amount of 2.5 mcg.

In an embodiment, the progestogen is administered in a daily amount of about 0.075 mg to about 5.0 mg, or about 0.3 mg to about 5.0 mg. In an embodiment, the progestogen is administered in a daily amount of about 0.075 mg to about 4.0 mg, or about 0.075 mg to about 2.0 mg, or about 0.075 mg to about 1.0 mg, or about 0.075 mg to about 0.15 mg, or about 0.4 mg to about 4.0 mg, or about 0.4 mg to about 3.0 mg, or about 0.5 mg to about 2 mg. In an embodiment, the progestogen is administered in a daily amount of about 0.075 mg, or about 0.1 mg, or about 0.15 mg, or about 0.2 mg, or about 0.25 mg, or about 0.3 mg, or about 0.4 mg, or about 0.5 mg, or about 0.6 mg, or about 0.7 mg, or about 0.8 mg, or about 0.9 mg, or about 1.0 mg, or about 1.1 mg, or about 1.2 mg, or about 1.3 mg, or about 1.4 mg, or about 1.5 mg, or any amount in between. In an embodiment, the progestogen is administered in a daily amount of about 1.0 mg.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 27 consecutive days of a 28-day cycle; and (b) a placebo for the remaining 1 day of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 26 consecutive days of a 28-day cycle; and (b) a placebo for the remaining 2 days of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 25 consecutive days of a 28-day cycle; and (b) a placebo for the remaining 3 days of the 28-day cycle. In an embodiment, the composition comprises about 2.5 mcg of an estrogen and about 1 mg of a progestogen. In an embodiment, the composition comprises 2.5 mcg of ethinyl estradiol and 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 24 consecutive days of a 28-day cycle; and (b) a placebo for the remaining 4 days of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 23 consecutive days of a 28-day cycle; and (b) a placebo for the remaining 5 days of the 28-day cycle. In an embodiment, the composition comprises about 2.5 mcg of an estrogen and about 1 mg of a progestogen. In an embodiment, the composition comprises 2.5 mcg of ethinyl estradiol and 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 22 consecutive days of a 28-day cycle; and (b) a placebo for the remaining 6 days of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 21 consecutive days of a 28-day cycle; and (b) a placebo for the remaining 7 days of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for 20 consecutive days of a 28-day cycle; and (b) a placebo for the remaining 8 days of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for at least 28 consecutive days up to about 84 consecutive days of a cycle; and (b) a placebo for about 1 to about 7 days following step (a) for the remainder of the cycle. The administration period for this cyclic monophasic regimen has an administration period of up to 91 days. In an embodiment, a new cycle begins following the completion of the preceding cycle. For example, a new 63-day begins following the completion of the preceding 63-day cycle. In an embodiment, the new cycle and the preceding cycle are identical in the number of days.

In an embodiment, the estrogen is administered in a daily amount of about 1.0 mcg to less than about 5.0 mcg. In an embodiment, the estrogen is administered in a daily amount of about 2.0 mcg to about 4.0 mcg, or about 2.25 to about 3.5 mcg, or about 2.25 mcg to about 3.0 mcg. In an embodiment, the estrogen is administered in a daily amount of about 1 mcg, or about 1.1 mcg, or about 1.2 mcg, or about 1.3 mcg, or about 1.4 mcg, or about 1.5 mcg, or about 1.6 mcg, or about 1.7 mcg, or about 1.8 mcg, or about 1.9 mcg, or about 2.0 mcg, or about 2.1 mcg or about 2.2 mcg, or about 2.3 mcg, or about 2.4 mcg, or about 2.5 mcg, or about 2.6 mcg, or about 2.7 mcg, or about 2.8 mcg, or about 2.9 mcg, or about 3.0 mcg, or about 3.1 mcg or about 3.2 mcg, or about 3.3 mcg, or about 3.4 mcg, or about 3.5 mcg, or about 3.6 mcg, or about 3.7 mcg, or about 3.8 mcg, or about 3.9 mcg, or about 4.0 mcg or about 4.1 mcg, or about 4.2 mcg, or about 4.3 mcg, or 4.4 mcg, or about 4.5 mcg, or any amount in between. In an embodiment, the estrogen is administered in a daily amount of 2.5 mcg.

In an embodiment, the progestogen is administered in a daily amount of about 0.075 mg to about 5.0 mg, or about 0.3 mg to about 5.0 mg. In an embodiment, the progestogen is administered in a daily amount of about 0.075 mg to about 4.0 mg, or about 0.075 mg to about 2.0 mg, or about 0.075 mg to about 1.0 mg, or about 0.075 mg to about 0.15 mg, or about 0.4 mg to about 4.0 mg, or about 0.4 mg to about 3.0 mg, or about 0.5 mg to about 2 mg. In an embodiment, the progestogen is administered in a daily amount of about 0.075 mg, or about 0.1 mg, or about 0.15 mg, or about 0.2 mg, or about 0.25 mg, or about 0.3 mg, or about 0.4 mg, or about 0.5 mg, or about 0.6 mg, or about 0.7 mg, or about 0.8 mg, or about 0.9 mg, or about 1.0 mg, or about 1.1 mg, or about 1.2 mg, or about 1.3 mg, or about 1.4 mg, or about 1.5 mg, or any amount in between. In an embodiment, the progestogen is administered in a daily amount of about 1.0 mg.

In an embodiment, the method of contraception for a female in need thereof is a cyclic monophasic regimen which includes administering, daily, the following: (a) a composition comprising about 1 mcg to less than about 5 mcg of an estrogen and about 0.075 mg to about 5 mg of a progestogen for at least 28 consecutive days, or about 42 days, or about 56 days, or about 63 days, up to about 84 consecutive days; and (b) a placebo for about 1 to about 7 days following step (a). In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the method of contraception for a female in need thereof is a cyclic multiphasic regimen which includes administering, daily, the following: (a) phase I composition comprising about 1 mcg to less than about 5 mcg of an estrogen and about 0.075 mg to about 5 mg of a progestogen for any one of about 20 to about 26 consecutive days of a 28-day cycle; (b) phase II composition comprising about 1 mcg to less than about 5 mcg of the estrogen, without a progestogen, for about 1 to about 6 consecutive days of the 28-day cycle following the administration of the phase I composition, such that at least one day remains in this 28-day cycle; and (c) a placebo for the remainder of the 28-day cycle.

In an embodiment, the phase I composition comprises about 2.5 mcg of an estrogen and about 1 mg of a progestogen. In an embodiment, the phase I composition comprises about 2.5 mcg of ethinyl estradiol and about 1 mg of norethindrone acetate. In an embodiment, the phase I composition comprises about 2.5 mcg of an estrogen and about 0.075 to about 0.15 mg of a progestogen. In an embodiment, the phase I composition comprises about 2.5 mcg of an ethinyl estradiol and about 0.075 to about 0.15 mg of a desogestrel.

In an embodiment, the phase II composition comprises about 2.5 mcg of an estrogen. In an embodiment, the phase II composition comprises about 2.5 mcg of ethinyl estradiol. The administration period for this multiphasic cyclic contraceptive method is based on a 28-day cycle. In an embodiment, a new cycle begins following the completion of the preceding cycle. For example, a new 28-day cycle begins following the completion of the preceding 28-day cycle. In an embodiment, the new cycle and the preceding cycle are identical in the number of days.

In an embodiment, the estrogen in each of phases I and II is administered in a daily amount of about 1.0 mcg to less than about 5.0 mcg. In an embodiment, the estrogen in each of phases I and II is administered in a daily amount of about 2.0 mcg to about 4.0 mcg, or about 2.25 mcg to about 3.5 mcg, or about 2.25 mcg to about 3.0 mcg. In an embodiment, the estrogen in each of phases I and II is administered in a daily amount of about 1 mcg, or about 1.1 mcg, or about 1.2 mcg, or about 1.3 mcg, or about 1.4 mcg, or about 1.5 mcg, or about 1.6 mcg, or about 1.7 mcg, or about 1.8 mcg, or about 1.9 mcg, or about 2.0 mcg, or about 2.1 mcg or about 2.2 mcg, or about 2.3 mcg, or about 2.4 mcg, or about 2.5 mcg, or about 2.6 mcg, or about 2.7 mcg, or about 2.8 mcg, or about 2.9 mcg, or about 3.0 mcg, or about 3.1 mcg or about 3.2 mcg, or about 3.3 mcg, or about 3.4 mcg, or about 3.5 mcg, or about 3.6 mcg, or about 3.7 mcg, or about 3.8 mcg, or about 3.9 mcg, or about 4.0 mcg or about 4.1 mcg, or about 4.2 mcg, or about 4.3 mcg, or 4.4 mcg, or about 4.5 mcg, or any amount in between. In an embodiment, the estrogen in each of phases I and II is administered in a daily amount of 2.5 mcg.

In an embodiment, the progestogen in phase I is administered in a daily amount of about 0.075 mg to about 5.0 mg, or about 0.3 mg to about 5.0 mg. In an embodiment, the progestogen in phase I is administered in a daily amount of about 0.075 mg to about 4.0 mg, or about 0.075 mg to about 2.0 mg, or about 0.075 mg to about 1.0 mg, or about 0.075 mg to about 0.15 mg, or about 0.4 mg to about 4.0 mg, or about 0.4 mg to about 3.0 mg, or about 0.5 mg to about 2 mg. In an embodiment, the progestogen in phase I is administered in a daily amount of about 0.075 mg, or about 0.1 mg, or about 0.15 mg, or about 0.2 mg, or about 0.25 mg, or about 0.3 mg, or about 0.4 mg, or about 0.5 mg, or about 0.6 mg, or about 0.7 mg, or about 0.8 mg, or about 0.9 mg, or about 1.0 mg, or about 1.1 mg, or about 1.2 mg, or about 1.3 mg, or about 1.4 mg, or about 1.5 mg, or any amount in between. In an embodiment, the progestogen in phase I is administered in a daily amount of about 1.0 mg. In an embodiment, no progestogen is administered in phase II.

In an embodiment, the method of contraception for a female in need thereof is a cyclic multiphasic regimen which includes administering, daily, the following compositions: (a) phase I composition for 24 consecutive days of a 28-day cycle comprising about 1 mcg to less than about 5 mcg of an estrogen and about 0.075 mg to about 5 mg of a progestogen; (b) phase II composition for 2 consecutive days of the 28-day cycle following the administration of the phase I composition, comprising about 1 mcg to less than about 5 mcg of the estrogen without a progestogen; and (c) a placebo for 2 consecutive days of the 28-day cycle following the administration of the phase II composition. In an embodiment, the phase I composition comprises about 2.5 mcg of an estrogen and about 1 mg of a progestogen. In an embodiment, the phase I composition comprises about 2.5 mcg of ethinyl estradiol and about 1 mg of norethindrone acetate. In an embodiment, the phase I composition comprises about 2.5 mcg of an estrogen and about 0.075 to about 0.15 mg of a progestogen. In an embodiment, the phase I composition comprises about 2.5 mcg of an ethinyl estradiol and about 0.075 to about 0.15 mg of a desogestrel. In an embodiment, the phase II composition comprises about 2.5 mcg of an estrogen. In an embodiment, the phase II composition comprises about 2.5 mcg of ethinyl estradiol.

In an embodiment, the method of contraception for a female in need thereof is a cyclic multiphasic regimen which includes administering, daily, the following compositions: (a) phase I composition for 24 consecutive days of a 28-day cycle comprising about 1 mcg to less than about 5 mcg of an estrogen and about 0.075 mg to about 5 mg of a progestogen; (b) phase II composition for 3 consecutive days of the 28-day cycle following the administration of the phase I composition, comprising about 1 mcg to less than about 5 mcg of the estrogen without a progestogen; and (c) a placebo for 1 day of the 28-day cycle following the administration of the phase II composition. In an embodiment, the phase I composition comprises about 2.5 mcg of an estrogen and about 1 mg of a progestogen. In an embodiment, the phase I composition comprises about 2.5 mcg of ethinyl estradiol and about 1 mg of norethindrone acetate. In an embodiment, the phase I composition comprises about 2.5 mcg of an estrogen and about 0.075 to about 0.15 mg of a progestogen. In an embodiment, the phase I composition comprises about 2.5 mcg of an ethinyl estradiol and about 0.075 to about 0.15 mg of a desogestrel. In an embodiment, the phase II composition comprises about 2.5 mcg of an estrogen. In an embodiment, the phase II composition comprises about 2.5 mcg of ethinyl estradiol.

In an embodiment, the method of contraception for a female in need thereof is a cyclic multiphasic regimen which includes administering, daily, the following compositions: (a) phase I composition for 24 consecutive days of a 28-day cycle comprising about 1 mcg to less than about 5 mcg of an estrogen and about 0.075 mg to about 5 mg of a progestogen; (b) phase II composition for 1 day of the 28-day cycle following the administration of the phase I composition, comprising about 1 mcg to less than about 5 mcg of the estrogen without a progestogen; and (c) a placebo for 3 consecutive days of the 28-day cycle following the administration of the phase II composition, comprising a. In an embodiment, the phase I composition comprises about 2.5 mcg of an estrogen and about 1 mg of a progestogen. In an embodiment, the phase I composition comprises about 2.5 mcg of ethinyl estradiol and about 1 mg of norethindrone acetate. In an embodiment, the phase I composition comprises about 2.5 mcg of an estrogen and about 0.075 to about 0.15 mg of a progestogen. In an embodiment, the phase I composition comprises about 2.5 mcg of an ethinyl estradiol and about 0.075 to about 0.15 mg of a desogestrel. In an embodiment, the phase II composition comprises about 2.5 mcg of an estrogen. In an embodiment, the phase II composition comprises about 2.5 mcg of ethinyl estradiol.

In an embodiment, the method of contraception for a female in need thereof, is a monophasic continuous regimen which includes administering, daily, the following: (a) a composition comprising about 1 mcg to less than about 5 mcg of an estrogen and about 0.075 mg to about 5 mg of a progestogen.

In an embodiment, the estrogen is administered in a daily amount of about 1.0 mcg to less than about 5.0 mcg. In an embodiment, the estrogen is administered in a daily amount of about 2.0 mcg to about 4.0 mcg, or about 2.25 mcg to about 3.5 mcg, or about 2.25 mcg to about 3.0 mcg. In an embodiment, the estrogen is administered in a daily amount of about 1 mcg, or about 1.1 mcg, or about 1.2 mcg, or about 1.3 mcg, or about 1.4 mcg, or about 1.5 mcg, or about 1.6 mcg, or about 1.7 mcg, or about 1.8 mcg, or about 1.9 mcg, or about 2.0 mcg, or about 2.1 mcg or about 2.2 mcg, or about 2.3 mcg, or about 2.4 mcg, or about 2.5 mcg, or about 2.6 mcg, or about 2.7 mcg, or about 2.8 mcg, or about 2.9 mcg, or about 3.0 mcg, or about 3.1 mcg or about 3.2 mcg, or about 3.3 mcg, or about 3.4 mcg, or about 3.5 mcg, or about 3.6 mcg, or about 3.7 mcg, or about 3.8 mcg, or about 3.9 mcg, or about 4.0 mcg or about 4.1 mcg, or about 4.2 mcg, or about 4.3 mcg, or 4.4 mcg, or about 4.5 mcg, or any amount in between. In an embodiment, the estrogen is administered in a daily amount of 2.5 mcg.

In an embodiment, the progestogen is administered in a daily amount of about 0.075 mg to about 5.0 mg, or about 0.3 mg to about 5 mg. In an embodiment, the progestogen is administered in a daily amount of about 0.075 mg to about 4.0 mg, or about 0.075 mg to about 2.0 mg, or about 0.075 mg to about 1.0 mg, or about 0.075 mg to about 0.15 mg, or about 0.4 mg to about 4.0 mg, or about 0.4 mg to about 3.0 mg, or about 0.5 mg to about 2 mg. In an embodiment, the progestogen is administered in a daily amount of about 0.075 mg, or about 0.1 mg, or about 0.15 mg, or about 0.2 mg, or about 0.25 mg, or about 0.3 mg, or about 0.4 mg, or about 0.5 mg, or about 0.6 mg, or about 0.7 mg, or about 0.8 mg, or about 0.9 mg, or about 1.0 mg, or about 1.1 mg, or about 1.2 mg, or about 1.3 mg, or about 1.4 mg, or about 1.5 mg, or any amount in between. In an embodiment, the progestogen is administered in a daily amount of about 1.0 mg.

In an embodiment, the estrogen and the progestogen can be in a combined single dosage form or a separate dosage form. In an embodiment, the dosage form can be a solid dosage form, a liquid dosage form, or a semisolid dosage form. In an embodiment, the dosage form can include, for example, a pill, an orally disintegrating tablet, a chewable tablet, a swallowing tablet, a capsule, a caplet, a drink, a syrup, a gel, or a strip.

In an embodiment, the dosage form is a vaginal ring or a patch, such that the vaginal ring or patch can be removed during any period where the active ingredient(s) are not administered in the methods disclosed herein. For example, in a continuous regimen, a patch or ring can be removed after a defined period (e.g., 90 days) and another ring or patch can be applied right away so as to provide uninterrupted administration of the active ingredient(s).

In an embodiment, the contraception method includes a kit comprising a package containing daily dosages of the estrogen with or without the progestogen, and the optional placebo, as described herein.

In an embodiment, the package may contain daily dosages of: (a) a composition comprising about 1 mcg to less than about 5 mcg of an estrogen and 0.075 mg to about 5 mg of a progestogen for about 20 to about 27 consecutive days of a 28-day cycle (e.g., about 20 to about 27 tablets, each including the aforementioned amounts of the estrogen and the progestogen, in, for example, a blister pack); and (b) a placebo (e.g., placebo tablet(s) in, for example, the blister pack, or, alternatively, empty blister(s) in the blister pack) for the remainder of the 28-day cycle. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the kit further comprises instructions for administering the daily dosages according to the method of contraception for a female in need thereof, being a cyclic monophasic regimen which includes administering, daily, the following: (a) a composition comprising about 1 mcg to less than about 5 mcg of an estrogen and about 0.075 mg to about 5 mg of a progestogen for about 20 to about 27 consecutive days of a 28-day cycle; and (b) a placebo for the remainder of the 28-day cycle.

In an embodiment, the package may contain daily dosages of: (a) a composition comprising about 1 mcg to less than about 5 mcg of an estrogen and 0.075 mg to about 5 mg of a progestogen for about 28 consecutive days up to 84 consecutive days (e.g., up to 84 tablets, each including the aforementioned amounts of the estrogen and the progestogen, in, for example, a blister pack, or multiple blister packs); and (b) a placebo (e.g., placebo tablet(s) in, for example, the blister pack, or, alternatively, empty blister(s) in the blister pack) for the up to 7 days. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the kit further comprises instructions for administering the daily dosages according to the method of contraception for a female in need thereof, being a cyclic monophasic regimen which includes administering, daily, the following: (a) a composition comprising about 1 mcg to less than about 5 mcg of an estrogen and about 0.075 mg to about 5 mg of a progestogen for at least 28 consecutive days up to about 84 consecutive days of a cycle; and (b) a placebo for about 1 to about 7 days following step (a) for the remainder of the cycle.

In an embodiment, the package may contain daily dosages of: (a) phase I composition comprising about 1 mcg to less than about 5 mcg of an estrogen and 0.075 mg to about 5 mg of a progestogen for about 20 to about 26 consecutive days of a 28-day cycle (e.g., about 20 to about 26 tablets, each including the aforementioned amounts of the estrogen and the progestogen, in, for example, a blister pack); (b) phase II composition comprising about 1 mcg to less than about 5 mcg of the estrogen, without a progestogen, for about 1 to about 6 consecutive days of the 28-day cycle following the administration of the phase I composition, such that at least one day remains in this 28-day cycle (e.g., about 1 to 6 tablets, each including the aforementioned amount of the estrogen and no progestogen, in, for example, the blister pack); and (c) a placebo (e.g., placebo tablet(s), or, alternatively, empty blister(s) in the blister pack) for the remainder of the 28-day cycle. In an embodiment, the phase I composition comprises about 2.5 mcg of an estrogen and about 1 mg of a progestogen. In an embodiment, the phase I composition comprises about 2.5 mcg of ethinyl estradiol and about 1 mg of norethindrone acetate. In an embodiment, the phase I composition comprises about 2.5 mcg of an estrogen and about 0.075 to about 0.15 mg of a progestogen. In an embodiment, the phase I composition comprises about 2.5 mcg of an ethinyl estradiol and about 0.075 to about 0.15 mg of a desogestrel. In an embodiment, the phase II composition comprises about 2.5 mcg of an estrogen. In an embodiment, the phase II composition comprises about 2.5 mcg of ethinyl estradiol.

In an embodiment, the kit further comprises instructions for administering the daily dosages according to the method of contraception for a female in need thereof, being a cyclic multiphasic regimen which includes administering, daily, the following compositions: (a) phase I composition comprising about 1 mcg to less than about 5 mcg of an estrogen and about 0.075 mg to about 5 mg of a progestogen for about 20 to about 26 consecutive days of a 28-day cycle; (b) phase II composition comprising about 1 mcg to less than about 5 mcg of the estrogen in the absence of the progestogen for about 1 to about 6 consecutive days of the 28-day cycle following the administration of the phase I composition; and (c) a placebo for the remainder of the 28-day cycle following the administration of the phase II composition.

In an embodiment, the package may contain daily dosages of: (a) a composition comprising about 1 mcg to less than about 5 mcg of an estrogen and about 0.075 mg to about 5 mg of a progestogen for a continuous regimen. In an embodiment, the composition comprises about 2.5 mcg of an estrogen and about 1 mg of a progestogen. In an embodiment, the composition comprises about 2.5 mcg of ethinyl estradiol and about 1 mg of norethindrone acetate. In an embodiment, the composition comprises about 2.5 mcg of an estrogen and about 0.075 to about 0.15 mg of a progestogen. In an embodiment, the composition comprises about 2.5 mcg of an ethinyl estradiol and about 0.075 to about 0.15 mg of a desogestrel.

In an embodiment, the kit further comprises instructions for administering the daily dosages according to the method of contraception for a female in need thereof, being a monophasic continuous regimen which includes administering, daily, the following: (a) a composition comprising about 1 mcg to less than about 5 mcg of an estrogen and about 0.075 mg to about 5 mg of a progestogen.

While the methods/regimens as disclosed herein are practiced by administration of the compositions in a numeric sequence with the estrogen/progestin containing composition(s) being used first, optionally, the estrogen only composition(s) or the optional placebo being used thereafter as discussed above, if packaging and/or other requirements dictate, the method and kit described herein can be employed as part of a larger scheme for contraception, or treatment of gynecological disorders. Reasonable variations, such as those which would occur to one of ordinary skill in the art, can be made herein without departing from the scope of the invention. For example, variations in time and dosage can be tolerated when medical considerations so dictate.

EXAMPLES

Specific embodiments will now be demonstrated by reference to the following examples. It should be understood that these examples are disclosed solely by way of illustrating the invention and should not be taken in any way to limit the scope of the present invention.

Example 1

The compositions employed in accordance with the invention will have the administration times and drug contents set forth in the following table.

TABLE 1

| Phase | Days | Norethindrone acetate (NA) (mg/day) | Ethinyl Estradiol (EE) (mcg/day) |
| --- | --- | --- | --- |
| I | 24 | 1.0 | 2.5 |
|   | 4 | 0 (placebo) | 0 (placebo) |

The norethindrone acetate (NA) and ethinyl estradiol (EE) are well known and readily available.

Example 2

The compositions employed in accordance with the invention will have the administration times and drug contents set forth in the following table.

TABLE 2

| Phase | Days | Norethindrone acetate (NA) (mg/day) | Ethinyl Estradiol (EE) (mcg/day) |
| --- | --- | --- | --- |
| I | 21 | 1.0 | 2.5 |
|   | 7 | 0 (placebo) | 0 (placebo) |

The norethindrone acetate (NA) and ethinyl estradiol (EE) are well known and readily available.

Example 3

The compositions employed in accordance with the invention will have the administration times and drug contents set forth in the following table.

TABLE 3

| Phase | Days | Norethindrone acetate (NA) (mg/day) | Ethinyl Estradiol (EE) (mcg/day) |
| --- | --- | --- | --- |
| I | 27 | 1.0 | 2.5 |
|   | 1 | 0 (placebo) | 0 (placebo) |

The norethindrone acetate (NA) and ethinyl estradiol (EE) are well known and readily available.

Example 4

The compositions employed in accordance with the invention will have the administration times and drug contents set forth in the following table.

TABLE 4

| Phase | Days | Norethindrone acetate (NA) (mg/day) | Ethinyl Estradiol (EE) (mcg/day) |
| --- | --- | --- | --- |
| I | 24 | 1.0 | 2.5 |
| II | 2 | 0 | 2.5 |
|   | 2 | 0 (placebo) | 0 (placebo) |

The norethindrone acetate (NA) and ethinyl estradiol (EE) are well known and readily available. In an embodiment, each of the phase I composition and phase II compositions are administered as oral dosage forms. In an embodiment, phase I composition is administered as a vaginal ring or a patch and the phase II composition is administered as an oral dosage form.

Example 5

The compositions employed in accordance with the invention will have the administration times and drug contents set forth in the following table.

TABLE 5

| Phase | Days | Norethindrone acetate (NA) (mg/day) | Ethinyl Estradiol (EE) (mcg/day) |
|---|---|---|---|
| I | 24 | 1.0 | 2.5 |
| II | 3 | 0 | 2.5 |
|  | 1 | 0 (placebo) | 0 (placebo) |

The norethindrone acetate (NA) and ethinyl estradiol (EE) are well known and readily available.

Example 6

The compositions employed in accordance with the invention will have the administration times and drug contents set forth in the following table.

TABLE 6

| Phase | Days | Norethindrone acetate (NA) (mg/day) | Ethinyl Estradiol (EE) (mcg/day) |
|---|---|---|---|
| I | 24 | 1.0 | 2.5 |
| II | 1 | 0 | 2.5 |
|  | 3 | 0 (placebo) | 0 (placebo) |

The norethindrone acetate (NA) and ethinyl estradiol (EE) are well known and readily available.

Example 7

The compositions employed in accordance with the invention will have the administration times and drug contents set forth in the following table.

TABLE 7

| Phase | Days | Norethindrone acetate (NA) (mg/day) | Ethinyl Estradiol (EE) (mcg/day) |
|---|---|---|---|
| I | 42 | 1.0 | 2.5 |
|  | 7 | 0 (placebo) | 0 (placebo) |

The norethindrone acetate (NA) and ethinyl estradiol (EE) are well known and readily available.

Example 8

The compositions employed in accordance with the invention will have the administration times and drug contents set forth in the following table.

TABLE 8

| Phase | Days | Norethindrone acetate (NA) (mg/day) | Ethinyl Estradiol (EE) (mcg/day) |
|---|---|---|---|
| I | 63 | 1.0 | 2.5 |
|  | 7 | 0 (placebo) | 0 (placebo) |

The norethindrone acetate (NA) and ethinyl estradiol (EE) are well known and readily available.

Example 9

The compositions employed in accordance with the invention will have the administration times and drug contents set forth in the following table.

TABLE 9

| Phase | Days | Norethindrone acetate (NA) (mg/day) | Ethinyl Estradiol (EE) (mcg/day) |
|---|---|---|---|
| I | Continuous without a placebo | 1.0 | 2.5 |

The norethindrone acetate (NA) and ethinyl estradiol (EE) are well known and readily available. For example, continuous regimen can be administered for up to 40 years.

In an embodiment, the regimens in the above Examples are administered daily via oral dosage forms. In an embodiment, norethindrone acetate (NA) and/or ethinyl estradiol (EE) in the Examples are administered via a vaginal ring or a patch.

For instance, in a multiphasic regimen, phase I is administered via a vaginal ring or a patch and phase II is administered via an oral dosage form. Alternatively, each phase is administered via a vaginal ring or a patch.

In an embodiment, if a vaginal ring is used, the vaginal ring may be removed after a certain period of time (e.g., 30 days or 90 days) followed by immediately inserting a new vaginal ring. In an embodiment, if a patch is used, the patch may be removed after a certain period of time (e.g., 30 days or 90 days) followed by immediately applying a new patch.

It should be noted that the tables are presented for illustrative purposes only. The substitution of functionally equivalent amounts and kinds of reagent(s) in these schemes is contemplated.

What is claimed is:

1. A method of contraception or treating one or more symptoms of endometriosis or fibroids for a female in need thereof comprising steps:
    a) administering to the female, daily, about 1 mcg to 2.5 mcg of ethinyl estradiol and about 0.075 mg to about 5 mg of a progestogen for about 20 to about 26 consecutive days of a 28-day cycle; and
    b) administering to the female, daily, about 1 mcg to 2.5 mcg of ethinyl estradiol in the absence of any progestogen for about 1 to about 6 consecutive days, of the 28-day cycle following the step a); and
    c) administering to the female, daily, a placebo for a remainder of the 28-day cycle.

2. The method of claim 1, wherein ethinyl estradiol and the progestogen in the step a) are administered for 24 consecutive days.

3. The method of claim 1, wherein ethinyl estradiol in the step b) is administered for 1 day.

4. The method of claim 1, wherein ethinyl estradiol in the step b) is administered for 2 consecutive days.

5. The method of claim 1, wherein ethinyl estradiol in the step b) is administered for 3 consecutive days.

6. The method of claim 1, wherein following the completion of the 28-day cycle, a new 28-day cycle begins.

7. The method of claim 1, wherein a daily amount of the progestogen administered in the step a) is about 1.0 mg.

8. The method of claim 1, wherein the progestogen is norethindrone acetate or desogestrel.

9. The method of claim 7, wherein the progestogen is norethindrone acetate.

10. The method of claim 1, wherein the female is not administered a gonadotropin-releasing hormone antagonist or a gonadotropin-releasing hormone agonist.

11. A method of contraception for a female in need thereof comprising steps:
   a) administering to the female, daily, 2.5 mcg of ethinyl estradiol and 1.0 mg of norethindrone acetate for 24 consecutive days of a 28-day cycle;
   b) administering to the female, daily, 2.5 mcg of ethinyl estradiol in the absence of any progestogen for 2 days of the 28-day cycle following the step a); and
   c) administering to the female, daily, a placebo for 2 days of the 28-day cycle following the step b).

* * * * *